United States Patent [19]
Schröder et al.

[11] 4,292,072
[45] Sep. 29, 1981

[54] NOVEL α-ISOCYANOCARBOXYLIC ACID COMPOUNDS AND PLANT GROWTH REGULANT COMPOSITIONS

[75] Inventors: Rolf Schröder, Wuppertal; Klaus Lürssen, Berg. Gladbach, both of Fed. Rep. of Germany

[73] Assignee: Bayer Aktiengesellschaft, Leverkusen, Fed. Rep. of Germany

[21] Appl. No.: 955,435

[22] Filed: Oct. 27, 1978

[30] Foreign Application Priority Data

Nov. 19, 1977 [DE] Fed. Rep. of Germany ....... 2751783

[51] Int. Cl.³ ............................................. A01N 37/34
[52] U.S. Cl. ........................................ 71/105; 71/70; 71/76; 71/77; 71/78; 260/464; 260/465 D; 260/465.4
[58] Field of Search .................. 71/105, 113; 260/464

[56] References Cited

U.S. PATENT DOCUMENTS

| | | | |
|---|---|---|---|
| 2,749,231 | 6/1956 | Ligett et al. | 71/106 |
| 3,277,171 | 10/1966 | Hopkins | 260/464 |
| 3,584,037 | 6/1971 | Gourse | 71/113 |
| 3,597,469 | 8/1971 | Bradwell | 71/113 |
| 3,673,237 | 6/1972 | Janiak | 71/106 |
| 3,773,824 | 11/1973 | Strong | 71/106 |
| 3,853,952 | 12/1974 | Kishida | 71/113 |
| 4,083,863 | 4/1978 | Brand | 260/464 |
| 4,098,600 | 7/1978 | Chupp | 71/105 |
| 4,118,412 | 10/1978 | Cleare et al. | 260/464 |

FOREIGN PATENT DOCUMENTS 2218009 11/1973 Fed. Rep. of Germany ...... 260/464
2349108 4/1975 Fed. Rep. of Germany ...... 260/464

OTHER PUBLICATIONS

Oediger et al., "Dialkylation in the Presence, etc.," (1976), CA84 No. 150,239h.

*Primary Examiner*—Glennon H. Hollrah
*Attorney, Agent, or Firm*—Sprung, Felfe, Horn, Lynch & Kramer

[57] ABSTRACT

New salts of α-isocyanocarboxylic acid of the formula

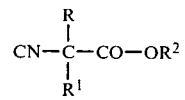

wherein
R is alkyl or phenyl,
R¹ is hydrogen, alkyl or phenylalkyl or
R and R¹ together represent an alkylene chain with at least 2 carbon atoms, and
R² is an alkali metal ion are provided. Such compounds are particularly efficacious in plant growth regulant activity and are more effective than conventional materials such as tri-n-butyl-tri-thiophosphoric acid ester and 2-chloroethanesulphinic acid.

5 Claims, No Drawings

NOVEL α-ISOCYANOCARBOXYLIC ACID COMPOUNDS AND PLANT GROWTH REGULANT COMPOSITIONS

The present invention relates to certain new α-isocyanocarboxylic acid compounds, to plant-growth regulants containing them and to methods of regulating plant growth utilizing them.

It is known that tri-n-butyl-trithiophosphoric acid ester, 2-chloroethanesulphinic acid and "Off-Shoot-T" ("Off-Shoot-T" is a commercially available plant-growth regulator based on fatty alcohols with 6, 8, 10 and 12 carbon atoms) have plant growth regulating properties. See U.S. Pat. Nos. 2,841,486 and 2,965,467; German Offenlegungsschrift (German published specification) No. 2,110,773 and Farm. Chem. Handbook 1975, Meister Publishing Co., Willoughby, Ohio, Pesticide Dictionary D 147.

However, the activity of these substances is not always completely satisfactory, especially at low application dosages and concentrations.

This invention provides, as new compounds, salts of α-isocyanocarboxylic acids, of the general formula

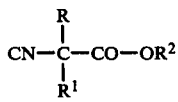  (I)

in which
R is alkyl or phenyl,
$R^1$ is hydrogen, alkyl or phenylalkyl or
R and $R^1$ together represent an alkylene chain with at least 2 carbon atoms, and
$R^2$ is an alkali metal ion.

The invention also relates to the use of the salts of the formula (I) as active compounds for regulating plant growth and to compositions containing the compounds (I).

Preferably, R represents straight-chain or branched alkyl with 1 to 6 (especially 1 to 4) carbon atoms or phenyl, $R^1$ represents hydrogen, straight-chain or branched alkyl with 1 to 4 (especially 1 or 2) carbon atoms, benzyl or phenylethyl or R and $R^1$ together represent an alkylene chain with 2 to 5 (especially 2 or 3) carbon atoms, and $R^2$ represents a sodium ion or potassium ion.

Surprisingly, the salts of the invention, of α-isocyanocarboxylic acids exhibit considerably more powerful plant growth regulating action than the substances known from the state of the art, that is to say tri-n-butyl-trithiophosphoric acid ester, 2-chloroethanesulphinic acid and "Off-Shoot-T", which are active compounds of high activity and the same type of action. The substances according to the invention thus represent a valuable enrichment of the art.

The invention also provides a process for the preparation of a salt of the formula (I) in which an α-isocyanocarboxylic acid alkyl ester of the general formula

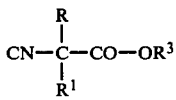  (II), in which
R and $R^1$ have the meaning stated above and
$R^3$ represents lower alkyl, preferably methyl or ethyl,
is reacted with an alkali metal hydroxide of the general formula $$HO-R^2 \quad \text{(III)},$$

in which $R^2$ has the meaning stated above, optionally in the presence of a solvent or dilutent.

If, for example, α-isocyanopropionic acid ethyl ester and potassium hydroxide are used as starting materials, the course of the reaction can be represented by the following equation:

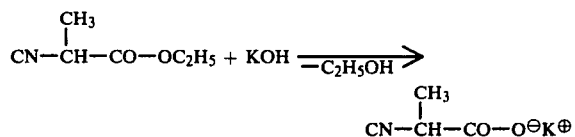

The formulae (II) and (III) provide general definitions of the α-isocyanocarboxylic acid alkyl esters and the alkali metal hydroxides to be used as starting materials.

Most of the α-isocyanocarboxylic acid alkyl esters (II) which can be used according to the invention are known. The compounds of the formula (II) which have not been previously described in the literature can be prepared by processes which are known in principle. Thus, for example, the methyl and ethyl esters of α-isocyano-acetic acid, α-isocyano-propionic acid and α-isocyano-valeric acid are obtained by the phosgene method described by J. Ugi (see Angewandte Chemie 77, 492 et seq. (1965)), and the compounds bis-alkylated on the carbon atoms in the α-position are obtained by the Schöllkopf method described, inter alia, in Chem. Ber. 108, 1,580 et seq. (1975).

Examples which may be mentioned of the compounds of the formula (II) which can be used according to the invention are: the methyl and ethyl esters of α-isocyano-propionic acid, α-isocyano-n-butyric acid, α-isocyano-n-valeric acid, α-isocyano-n-caproic acid, α-isocyano-iso-valeric acid, α-isocyano-iso-butyric acid, α-isocyano-α-methylbutyric acid, α-isocyano-α-methyl-n-valeric acid, α-isocyano-α-methyl-caproic acid, α-isocyano-α-ethyl-n-butyric acid, α-isocyano-α-ethyl-n-valeric acid, α-isocyano-α-phenylmethyl-propionic acid and α-isocyano-α-(2-phenylethyl)-propionic acid and the methyl and ethyl ester of 1-isocyano-cyclopropylcarboxylic acid.

The alkali metal hydroxides of the formula (III) which can also be used as starting materials are known. Examples which may be mentioned are sodium hydroxide and potassium hydroxide.

The process for the preparation of the compounds according to the invention can be carried out using a suitable solvent or diluent. Possible solvents and diluents are virtually all the inert organic solvents, especially aliphatic or aromatic, optionally chlorinated hydrocarbons, such as benzene, toluene, xylene, methylene chloride, chloroform, carbon tetrachloride and chlorobenzene; ethers, for example diethyl ether, dibutyl ether and dioxan; and alcohols, such as ethanol. The reaction according to the invention can also be carried out in a mixture of any of the above-mentioned solvents.

The reaction temperature can be varied within a relatively wide range. In general, the reaction is carried out at from −10° to +60° C., preferably at from 0° to 20° C.

In general, the reaction according to the invention is carried out under normal pressure.

In carrying out the process according to the invention for the preparation of a compound of the formula (I), the alkali metal hydroxide (III) is preferably added in 10 to 30% excess to the α-isocyanocarboxylic acid alkyl ester, optionally in one of the solvents indicated. After stirring the mixture for several hours, the product is filtered off, washed and dried.

The compounds are obtained in crystalline form and are characterized by their melting point.

Examples which may be mentioned of the salts of the formula (I) are: sodium α-isocyano-propionate, potassium α-isocyano-propionate, sodium α-isocyano-butyrate, potassium α-isocyano-butyrate, sodium α-isocyano-n-valerate, potassium α-isocyano-n-valerate, sodium α-isocyano-iso-valerate, potassium α-isocyano-iso-valerate, sodium α-isocyano-iso-butyrate, potassium α-isocyano-iso-butyrate, sodium α-isocyano-α-methyl-butyrate, potassium α-isocyano-α-methyl-butyrate, sodium α-isocyano-α-ethyl-butyrate, potassium α-isocyano-α-ethyl-butyrate, sodium α-isocyano-α-phenylmethyl-propionate, sodium α-isocyano-α-(2-phenethyl)-propionate, potassium α-isocyano-α-(2-phenethyl)-propionate, potassium α-isocyano-α-phenylmethyl-propionate, sodium 1-isocyano-cyclopropylcarboxylate and potassium 1-isocyano-cyclopropylcarboxylate.

As already mentioned, the salts, according to the invention, of α-isocyanocarboxylic acids are distinguished by a plant-growth regulating action.

Some of the compounds also have a herbicidal action. For this reason, the compounds according to the invention can be successfully employed in plant protection.

The compounds according to the present invention engage in the metabolism of plants and can therefore be employed as growth regulators.

Experience to date of the mode of action of plant growth regulators has shown that an active compound can exert one or several different actions on plants. The actions of the compounds depend essentially on the point in time at which they are used, relative to the stage of development of the seed or of the plant, and on the amounts of active compound applied to the plants or their environment and the way in which the compounds are applied. In every case, growth regulators are intended positively to influence the crop plants in the desired manner.

Plant growth-regulating compounds can be employed, for example, to inhibit vegetative plant growth. Such inhibition of growth is inter alia of economic interest in the case of grasses since, by repressing the growth of grass, it is possible, for example, to reduce the frequency of cutting the grass in ornamental gardens, parks and sports grounds or at verges. The inhibition of growth of herbaceous and woody plants at verges and in the vicinity of overland pipelines or, quite generally, in areas in which heavy growth is undesired, is also of importance.

The use of growth regulators to inhibit the growth in length of cereals is also important, since by shortening the stem the danger of lodging of the plants before harvesting is reduced or completely eliminated. Furthermore, growth regulators can strengthen the stem of cereals, which can counteract lodging.

In the case of many crop plants, inhibition of the vegetative growth permits denser planting of the crop, so that a greater yield per area of ground can be achieved.

A further mechanism of increasing the yield by means of growth inhibitors is based on the fact that the nutrients benefit blossoming and fruit formation to a greater extent, whilst vegetative growth is restricted.

Promotion of vegetative growth can also frequently be achieved with growth regulators. This is of great utility if it is the vegetative parts of the plants which are harvested. Promoting the vegetative growth can, however, also simultaneously lead to a promotion of generative growth, so that, for example, more fruit, or larger fruit, is formed.

Increases in yield can in some cases also be achieved by affecting the plant metabolism, without noticeable changes in vegetative growth. Growth regulators can furthermore produce a change in the composition of the plants so as to bring about better quality of the harvested products. Thus it is possible, for example, to increase the content of sugar in sugar beet, sugar cane, pineapples and citrus fruit or to increase the protein content in soya or cereals.

Parthenocarpous fruit can be formed under the influence of growth regulators. Furthermore, the gender of the flowers can be influenced.

Using growth regulators it is also possible favourably to influence the production or the efflux of secondary plant materials. The stimulation of latex flow in rubber trees may be mentioned as an example.

During the growth of the plant, lateral branching can also be increased, by using growth regulators, through chemical breaking of the apical dominance. There is interest in this, for example, in the case of plant propagation by cuttings. However, it is also possible to inhibit the growth of side shoots, for example to prevent the formation of side shoots in tobacco plants after decapitation and thus to promote leaf growth.

The amount of leaf on plants can be controlled, under the influence of growth regulators, so that defoliation of the plants at a desired point in time is achieved. Such defoliation is of interest to facilitate mechanical harvesting, for example of grapes or cotton, or to lower the transpiration at a point in time at which the plant is to be transplanted.

Premature shedding of fruit can be prevented by the use of growth regulators. However, it is also possible to promote the shedding of fruit—for example in the case of table fruit—in the sense of a chemical thinning out, up to a certain degree. Growth regulators can also be used to reduce the force required to detach the fruit from crop plants at harvest time so as to permit mechanical harvesting of the plants or facilitate manual harvesting.

Using growth regulators it is furthermore possible to achieve an acceleration or retardation of ripening of the harvest product, before or after harvesting. This is of particular advantage since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators it is also possible to influence the latent period of seeds or buds of plants, that is to say the endogenic annual rhythm, so that the plants, such as, for example, pineapple or decorative plants in nurseries, germinate, shoot or blossom at a time at which they normally show no readiness to do so.

Using growth regulators it is also possible to achieve a delay in the shooting of buds or the germination of seeds, for example to avoid damage by late frosts in regions where frost is a hazard.

Growth regulators can also produce halophilism in crop plants. This provides the preconditions for being able to cultivate plants on soils containing salt.

Using growth regulators, it is also possible to induce frost resistance and drought resistance in plants.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations as a mixture with other active compounds, such as fungicides, insecticides, acaricides and herbicides, and also as a mixture with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They may be used in the customary manner, for example by watering, spraying, atomising, scattering, dusting, foaming and gassing. Furthermore it is possible to apply the active compounds in accordance with the ultra-low-volume method, to spread the active compound preparation or the active compound itself on plants or parts of plants or to inject the active compound preparation or the active compound itself into the soil. It is also possible to treat the seeds of plants.

The active compound concentrations can be varied within a substantial range. In general 0.01 to 50 kg, preferably 0.05 to 10 kg, of active compound are employed per hectare of soil surface.

The present invention also provides a plant-growth-regulating composition containing as active ingredient a compound of the present invention in admixture with a solid or liquefied gaseous diluent or carrier or in admixture with a liquid diluent or carrier containing a surface-active agent.

The present invention also provides a method of regulating the growth of plants which comprises applying to the plants, or to a habitat thereof, a compound of the present invention alone or in the form of a composition containing as active ingredient a compound of the present invention in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

The Examples which follow illustrate the activity of the substances according to the invention as growth regulators without excluding the possibility of further applications as growth regulators.

In these Examples, the compounds according to the present invention are each identified by the number (given in brackets) of the corresponding preparative Example, which will be found later in this specification.

The known comparison compounds are identified as follows:

(A)=(CH$_3$—CH$_2$—CH$_2$—CH$_2$—S)$_3$PO (tri-n-butyl-trithiophosphoric acid ester)

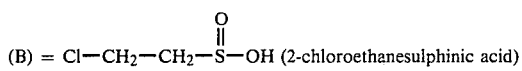
(B) = Cl—CH$_2$—CH$_2$—S—OH (2-chloroethanesulphinic acid)

(C)=Off-Shoot-T (a plant-growth regulator based on fatty alcohols with 6, 8, 10 and 12 carbon atoms).

EXAMPLE A

Defoliation of cotton plants and desiccation of cotton leaves

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 1 week, the shedding of leaves and the desiccation of the leaves was rated. The results were compared with those of the untreated control plants.

In this test, compounds (1) and (5) caused substantially greater shedding of leaves and greater desiccation of the leaves than substance (A), known from the prior art.

EXAMPLE B

Acceleration of ripening of tobacco

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Tobacco plants were grown in a greenhouse until they flowered. The flower heads were removed. In this stage, the plants were sprayed with the preparations of active compound until dripping wet. After 1 week, the coloration of the leaves was compared with the untreated control plants.

In this test, compound (5) caused substantially more rapid ripening than substance (B), known from the prior art.

EXAMPLE C

Acceleration of ripening of tomatoes

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Tomato plants were grown outdoors in the usual manner until about half of the fruit was red-coloured. In this stage, the plants were sprayed with the preparations of active compound until dripping wet. After 2 weeks, the coloration of the fruit was evaluated. Untreated control plants were used for comparison.

Compound (5) caused substantially more rapid ripening than substance (B), known from the prior art.

EXAMPLE D

Inhibition of growth of side shoots of tobacco

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Tobacco plants were grown in a greenhouse until the 7th foliage leaf had unfolded. In this stage, the apical vegetative tips of the plants were removed and the plants were sprayed with the preparations of active compound until dripping wet. After 3 weeks, the side shoots of the plants were broken off and weighed. The weight of the side shoots of the treated plants was compared with that of the untreated control plants.

In this test, compound (5) caused substantially better inhibition of the growth of side shoots than substance (C), known from the prior art.

EXAMPLE E

Inhibition of growth of soya beans

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Soya bean plants were grown in a greenhouse until the first secondary leaf had unfolded completely. In this stage, the plants were sprayed with the preparations of active compound until dripping wet. After 3 weeks, the additional growth of the treated plants was compared with the additional growth of the untreated control plants.

In this test compound (4) caused a substantially greater inhibition of growth than substance (B), known from the prior art.

EXAMPLE F

Inhibition of growth of cotton

Solvent: 30 parts by weight of dimethylformamide

Emulsifier: 1 part by weight of polyoxyethylene sorbitan monolaurate

To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the treated plants was compared with the additional growth of the untreated control plants.

In this test, compound (5) caused a substantially greater inhibition of growth than substance (B), known from the prior art.

EXAMPLE G

Inhibition of growth of wheat

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Wheat plants were grown to the 2-leaf stage in a greenhouse. In this stage, the plants were sprayed with the preparations of active compound until dripping wet. After 3 weeks, the additional growth of the treated plants was compared with the additional growth of the untreated control plants.

In this test, compounds (1) and (5) caused a substantially greater inhibition of growth than substance (B), known from the prior art.

EXAMPLE H

Inhibition of growth of barley

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Barley plants were grown to the 2-leaf stage in a greenhouse. In this stage, the plants were sprayed with the preparations of active compound until dripping wet. After 3 weeks, the additional growth of the treated plants was compared with the additional growth of the untreated control plants.

In this test, compound (5) caused a substantially greater inhibition of growth than substance (B), known from the prior art.

EXAMPLE I

Promotion of growth of cotton

Solvent: 30 parts by weight of dimethylformamide
Emulsifier: 1 part by weight of polyoxyethylene sorbitan monolaurate To produce a suitable preparation of active compound, 1 part by weight of active compound was mixed with the stated amount of solvent and emulsifier and the mixture was made up to the desired concentration with water.

Cotton plants were grown in a greenhouse until the 5th foliage leaf had unfolded completely. In this stage, the plants were sprayed with the preparations of active compound until dripping wet. After 3 weeks, the additional growth of the treated plants was compared with the additional growth of the untreated control plants.

In this test, compounds (1), (3) and (4) greatly promoted growth.

PREPARATIVE EXAMPLES

EXAMPLE 1:

A solution of 24.6 g (0.44 mol) of potassium hydroxide in 500 ml of ethanol was added to a solution of 50.8 g (0.4 mol) of α-isocyanopropionic acid ethyl ester in 300 ml of ether at about 5° C. in the course of 15 minutes, whilst cooling and stirring. The mixture was then stirred at room temperature for a further 6 hours, the product was filtered off and rinsed with 100 ml of ether and the residual traces of solvent were removed in vacuo in a desiccator. 44 g (81% of theory) of the potassium salt of α-isocyanopropionic acid were isolated in the form of a white powder with a melting point of 219° C. (decomposition).

The following compounds of the formula

were synthesized analogously to Example 1:

| Example No. | R | $R^1$ | $R^2$ | Yield (% of theory) | Melting point (°C.) |
|---|---|---|---|---|---|
| 2 | $C_3H_7$—iso | H | K | 99 | 215 (decomposition) |
| 3 | $CH_3$ | $CH_3$ | K | 69 | 200 |
| 4 | $CH_3$ | ⟨⟩—$CH_2$— | K | 35 | 235 |
| 5 | —$CH_2$—$CH_2$— | | K | 86 | 225 |
| 6 | —$CH_2$—$CH_2$— | | Na | 85 | 250 (decomposition) |

It will be understood that the specification and examples are illustrative but not limitative of the present invention and that other embomdiments within the spirit and scope of the invention will suggest themselves to those skilled in the art.

What is claimed is:

1. Plant growth regulant compositions comprising an agriculturally acceptable carrier and, in effective amounts, a salt of α-isocyanocarboxylic acid of the formula

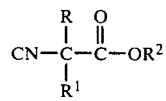

wherein R and R$^1$ together represent an alkylene chain of 2 carbon atoms and R$^2$ is an alkali metal ion.

2. Method of regulating plant growth which method comprises applying to plants, or other habitat, a plant growth regulatingly effective amount of a salt of α-isocyanocarboxylic acid as claimed in claim 1.

3. Method as claimed in claim 2 wherein said salt is selected from potassium 1-isocyano-cyclopropylcarboxylate or sodium 1-isocyano-cyclopropylcarboxylate.

4. Method as claimed in claim 2 wherein said salt is applied to an area of plant cultivation in an amount of 0.01 to 50 kg/hectare.

5. Method as claimed in claim 4 wherein said salt is applied to an area of plant cultivation in an amount of 0.05 to 10 kg/hectare.

* * * * *